(12) United States Patent
Tillman, Jr.

(10) Patent No.: US 6,783,578 B2
(45) Date of Patent: Aug. 31, 2004

(54) AIR PURIFICATION UNIT

(75) Inventor: Bernard William Tillman, Jr., Houston, TX (US)

(73) Assignee: Isolate, Inc., Houston, TX (US)

(*) Notice: Subject to any disclaimer, the term of this patent is extended or adjusted under 35 U.S.C. 154(b) by 0 days.

(21) Appl. No.: 10/321,251

(22) Filed: Dec. 17, 2002

(65) Prior Publication Data

US 2004/0112221 A1 Jun. 17, 2004

(51) Int. Cl.[7] .............................................. B01D 50/00
(52) U.S. Cl. ........................... 96/224; 55/356; 55/410; 55/472; 55/473
(58) Field of Search ............................. 96/224; 55/356, 55/410, 467, 472, 473

(56) References Cited

U.S. PATENT DOCUMENTS

| | | | |
|---|---|---|---|
| 1,170,526 A | | 2/1916 | Gaither |
| 2,611,679 A | * | 9/1952 | Haulenbeek et al. .......... 96/224 |
| 2,945,554 A | | 7/1960 | Berly |
| 3,217,470 A | | 11/1965 | Omohundro |
| 3,827,862 A | | 8/1974 | Berlant |

(List continued on next page.)

OTHER PUBLICATIONS

Isolate, Inc., ISO®–HEPA/UVC HEPA Air Filtration Units for Room Microbiological Control, Nov. 2001, 1 page (2 sided), distributed in the U.S. by isolate, Inc.

Primary Examiner—Robert A. Hopkins
(74) Attorney, Agent, or Firm—Haynes and Boone LLP; Todd Mattingly

(57) ABSTRACT

An air purification apparatus is disclosed that includes a HEPA or ULPA cartridge filter having mounted axially therein an UV lamp extending from a closed end of the cartridge. An air channeling housing is provided for removably mounting the combination filter and lamp assembly for ingress of an air stream through the open end of the combination filter and lamp assembly and for egress of the air stream through the filter medium. A fan can be mounted in the housing either upstream or downstream of the combination filter to provide the means for flowing air through the housing for decontamination by both the filter and UV irradiation provided by the combination filter and lamp assembly. With this arrangement, all contaminants trapped on the filter are within the combination filter and lamp assembly for constant illumination by the UV lamp to destroy bacteria both in the incoming air stream and while resident on the interior of the filter assembly. As disclosed, when the apparatus is installed in an air stream, the air moves into the tubular filter where contaminants are killed by the UV lamp either before or after capture on the interior of the tubular filter before egress through the filter medium.

24 Claims, 6 Drawing Sheets

U.S. PATENT DOCUMENTS

| | | |
|---|---|---|
| 4,102,654 A | 7/1978 | Bommer |
| 4,118,191 A | 10/1978 | Bohnensieker |
| 4,750,917 A | 6/1988 | Fujii |
| 4,988,372 A | 1/1991 | Meline |
| 5,047,072 A | 9/1991 | Todd |
| 5,074,894 A | 12/1991 | Nelson |
| 5,185,015 A | 2/1993 | Searle |
| 5,190,659 A | 3/1993 | Wang |
| 5,225,167 A | 7/1993 | Wetzel |
| 5,236,595 A | 8/1993 | Wang |
| 5,256,299 A | 10/1993 | Kuryiko |
| 5,330,722 A | 7/1994 | Pick |
| 5,334,347 A | 8/1994 | Hollander |
| 5,399,319 A | 3/1995 | Reavis |
| 5,523,057 A | 6/1996 | Mazzill |
| 5,612,001 A | 3/1997 | Matschke |
| 5,616,172 A * | 4/1997 | Tuckerman et al. ........... 96/16 |
| 5,817,276 A | 10/1998 | Culbert |
| 5,866,076 A | 2/1999 | Hodgetts |
| 5,884,500 A | 3/1999 | Wetzel |
| 5,997,619 A | 12/1999 | Carey |
| 6,053,968 A | 4/2000 | Miller |
| 6,193,894 B1 | 2/2001 | Hollander |
| 6,221,314 B1 | 4/2001 | Bigelow |
| 6,245,293 B1 | 6/2001 | Scheir |
| 6,284,025 B1 | 9/2001 | Kreisberg et al. |
| 6,372,186 B1 | 4/2002 | Hering |
| 6,589,489 B2 * | 7/2003 | Morrow et al. ........... 422/186.3 |
| 6,666,912 B1 * | 12/2003 | Yan ............................ 96/224 |
| 2001/0006162 A1 | 7/2001 | Culbert |

* cited by examiner

US 6,783,578 B2

AIR PURIFICATION UNIT

FIELD OF INVENTION

The present application relates to devices for removing, capturing and rendering harmless bio-contaminants from air streams.

BACKGROUND OF THE INVENTION

Filters have long been used to remove contaminants in air handling systems. There have also been attempts to use ultra violet or UV lamps to destroy bacteria on a variety of surfaces, including filter surfaces. There is a long felt but unmet need for an effective purification unit that combines the bacteria destroying affects of UV radiation with effective purification by filtering in a more efficient and effective manner and simultaneously killing bacteria in the air stream and on the filtering medium.

SUMMARY OF THE INVENTION

The present invention provides a unique, simple combination filter and ultra-violet lamp assembly that includes a high purification filter and high power UV radiation lamp in a single replaceable and disposable unit capable of being easily installed into an existing air handling system, designed into a new air handing unit or for use in a stand alone room air purifier. The invention includes a tubular filter medium, preferably a pleated HEPA or ULPA filter mounted by opposing supporting end plates with one plate adapted for mounting a UV lamp and fixture in air sealed relationship to the filter medium such that the lamp is inside and surrounded by the filter medium and the power connecting portion of the fixture is outside the supporting end plate. The other supporting end plate has an air ingress opening therethrough.

According to one embodiment, a self contained air purification unit is provided for replaceably mounting the filter and lamp assembly within an air handling system. The unit includes a housing having at least one removable wall for access to the filter and lamp assembly for installation and removal of the assembly. The housing is constructed to channel air flow through the housing for passage into the filter and lamp assembly and out through the filter medium. According to one aspect of the invention, a fan and motor assembly is mounted within the housing to draw air through the filter and in another the fan and motor assembly is mounted within the housing to push air through the filter.

DETAILED DESCRIPTION OF ILLUSTRATIVE EMBODIMENTS

Figure 1:
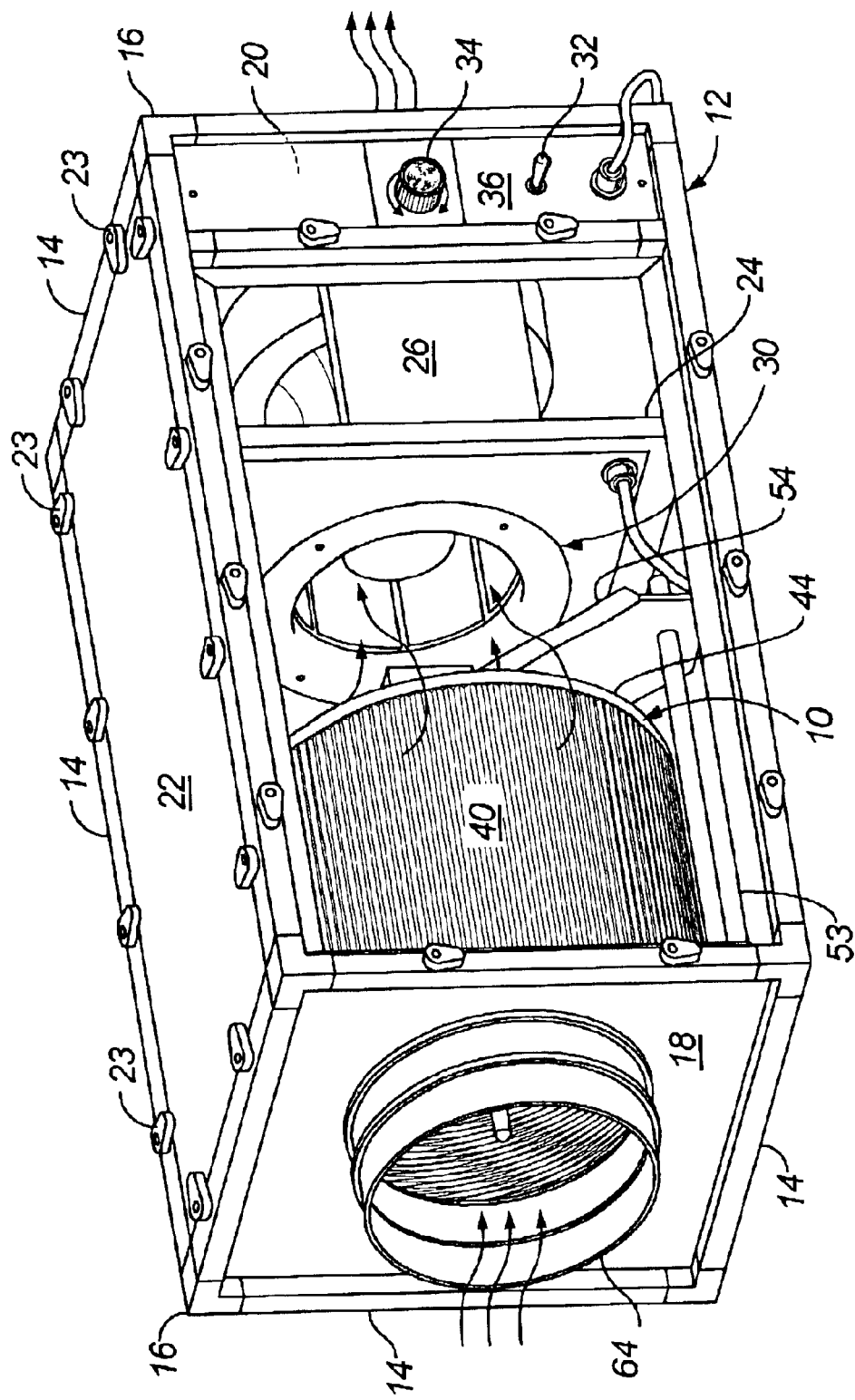
FIG. 1 is a side perspective view of an exemplary embodiment of the invention suitable for mounting within the duct of an air handling system.

The Drawing illustrates an embodiment of the invention that features a combination filter and UV lamp assembly 10 mounted within a housing 12 with a fan mounted downstream of the combination filter and lamp assembly. The illustrated embodiment is configured to be suitable for mounting within an existing air handling system or for mounting within the ducting system for a newly constructed air handling system. As can be appreciated, the invention can easily be adapted for use as a stand alone room purification unit by adding legs and/or casters to support the unit housing in an upright position.

Figure 2:
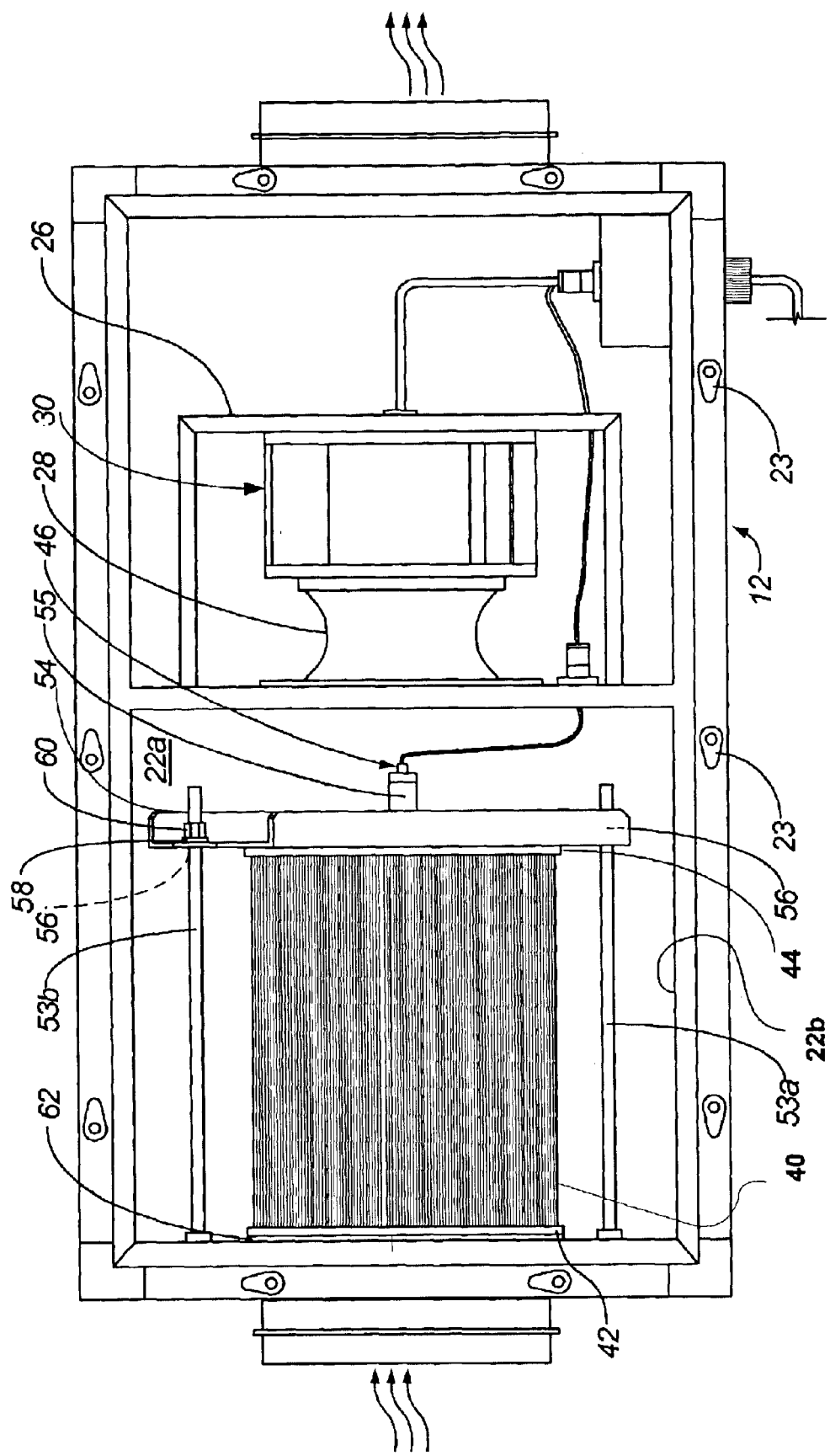
FIG. 2 is a top perspective view of the embodiment of FIG. 1.

FIGS. 1 and 2 illustrate an embodiment of the invention constructed for either adding into an existing air handling system or including in a newly constructed system to remove air borne contaminants before or after air is delivered to or from rooms served by the system. The invention as illustrated includes a replaceable combination filter and UV lamp assembly 10 mounted within a generally rectangular housing.

With reference to the side view of FIG. 1 and the top view of FIG. 2, as illustrated, the housing 12 can be conveniently constructed of frame pieces 14 joined at their corners by connectors 16. The housing provides the means for channeling air for removal and decontamination of air borne particulates and bacterial contaminants by the combination filter and UV lamp assembly 10. As shown, the housing 12 includes a first end panel 18 for air ingress to the housing and a second end panel 20 for air egress from the housing. As will be appreciated, the location of the air ingress and air egress openings depend on the configuration of surrounding ductwork of an air handling system.

The housing 12 further includes side panels 22 which are conveniently mounted to the frame by way of swivel retainers 23. As best shown in FIG. 2, the housing 12 also includes suitably placed and secured internal structural members such as divider support wall 24. U bracket 26 is conveniently mounted to the divider support wall 24 to mount fan and motor assembly 30 and inlet venturi 28 within the housing 12, in axial alignment with the combination filter and UV lamp assembly 10. As shown in FIG. 1, a fan switch 32 and fan speed controller 34 (FIG. 1) are conveniently mounted to control mounting panel 36. In FIGS. 1 and 2, different ones of the side panels 22 have been removed to show the interior of the housing 12. FIG. 1 shows the side panel removed as it might be when the combination filter and UV lamp assembly 10 is being installed or replaced within an air handling system.

Figure 3:
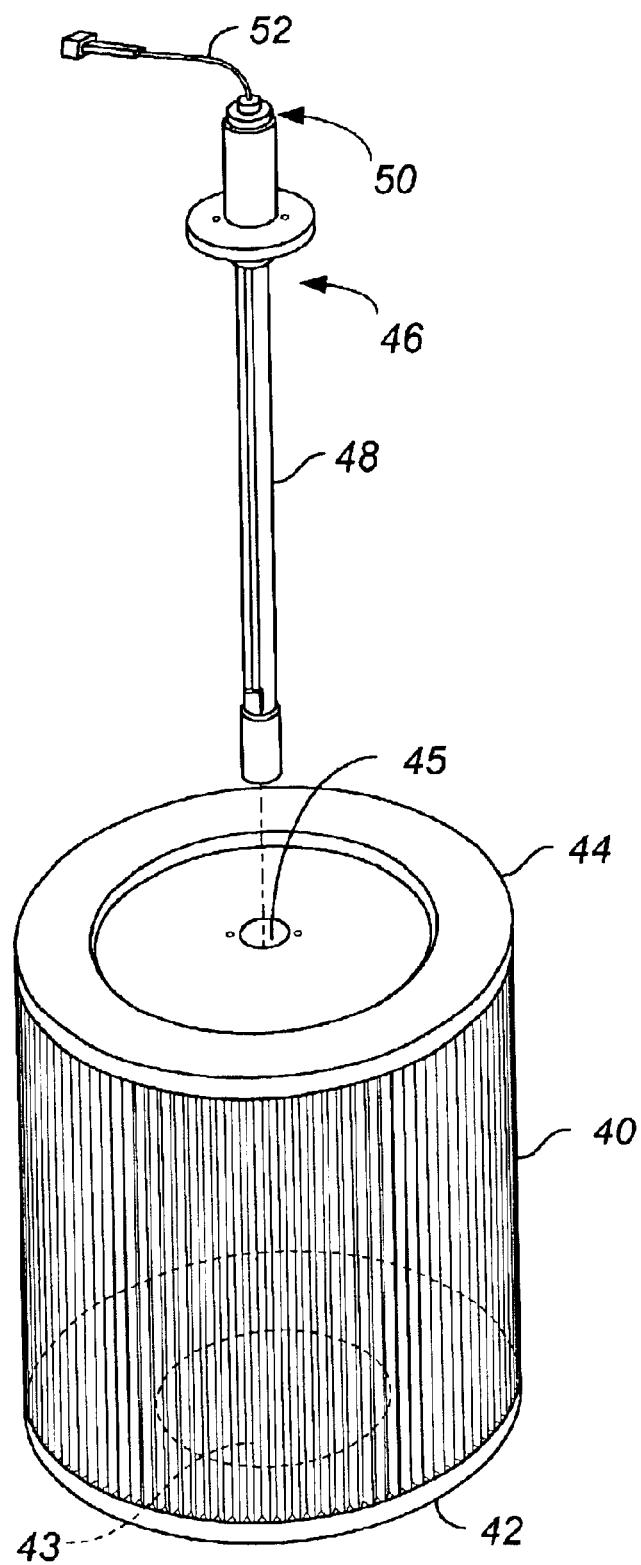
FIG. 3 is an exploded assembly view of the filter and lamp assembly of FIG. 1.

As best shown in FIG. 3, the combination filter and UV lamp assembly 10 includes a filter medium 40 disposed between opposing circular, imperforate filter medium support plates such as air entry plate 42 and lamp mounting plate 44. An annular, cartridge type disposable HEPA (high efficiency particulate air) filter can conveniently be adapted for use with this invention. For purposes of this invention, air entry plate 42 includes an opening 43 which provides the entry point for contaminated air into the annular space within the filter medium 40. The filter retaining plate 44 is adapted to provide opening 45 sized to receive UV lamp 46. The lamp 46 includes bulb 48 secured in operative connection to lamp fixture 50 having power connector 52 for connection to a power source for illuminating the lamp 46.

As best shown in FIG. 2, to enable the combination filter and UV lamp assembly 10 to be removably secured within the housing 12, threaded rods 53a and 53b extend laterally, inwardly from the air ingress end panel 18 of the housing 12, adjacent housing sidewalls, such as housing back wall 22a and housing bottom wall 22b respectively. The rods 53a and 53b are sized to extend from the end panel 18 to a point beyond the filter retaining, lamp mounting plate 44 to cooperate with bracket 54 to secure combination filter and ultraviolet lamp assembly 10 within the housing 12. The bracket 54 includes a central clearance hole 55 (see FIG. 4) for receiving the lamp fixture 50 and distal clearance holes 56 for receiving the rods 53a and 53b. Lock washers 58 and hex nuts 60, threaded on the rods 53a and 53b, function to secure the combination filter and ultraviolet lamp assembly 10 against the air ingress housing panel 18 with gasket 62 compressed between the filter's air entry plate 42 and the housing's air ingress end panel 18. As can be appreciated, the means for removably securing the combination filter and UV lamp assembly 1—within the housing 12 can include any known method for holding a part in compression against a plate, such as a spring type latch.

As can now be appreciated, the housing 12 not only provides the structure for mounting components of the unit but channels an incoming air stream to assure that air flow is through the filter medium 40 from inside to the outside so that contaminants are trapped within the combination filter and lamp assembly 10. With this arrangement, the UV illumination produced by the lamp 46 can continuously kill bacteria, mold, or other microorganisms in the incoming air stream and kill all such material trapped by and resident on the inside of the filter medium 40. For purposes of air channeling in the embodiment shown in FIGS. 1 and 2, each of the ingress end panel 18 and egress end panel 20 can conveniently have mounted thereon a connecting collar, such as collar 64, for air sealing engagement with the air handling ducts in which the housing 12 will be installed.

Figure 4:
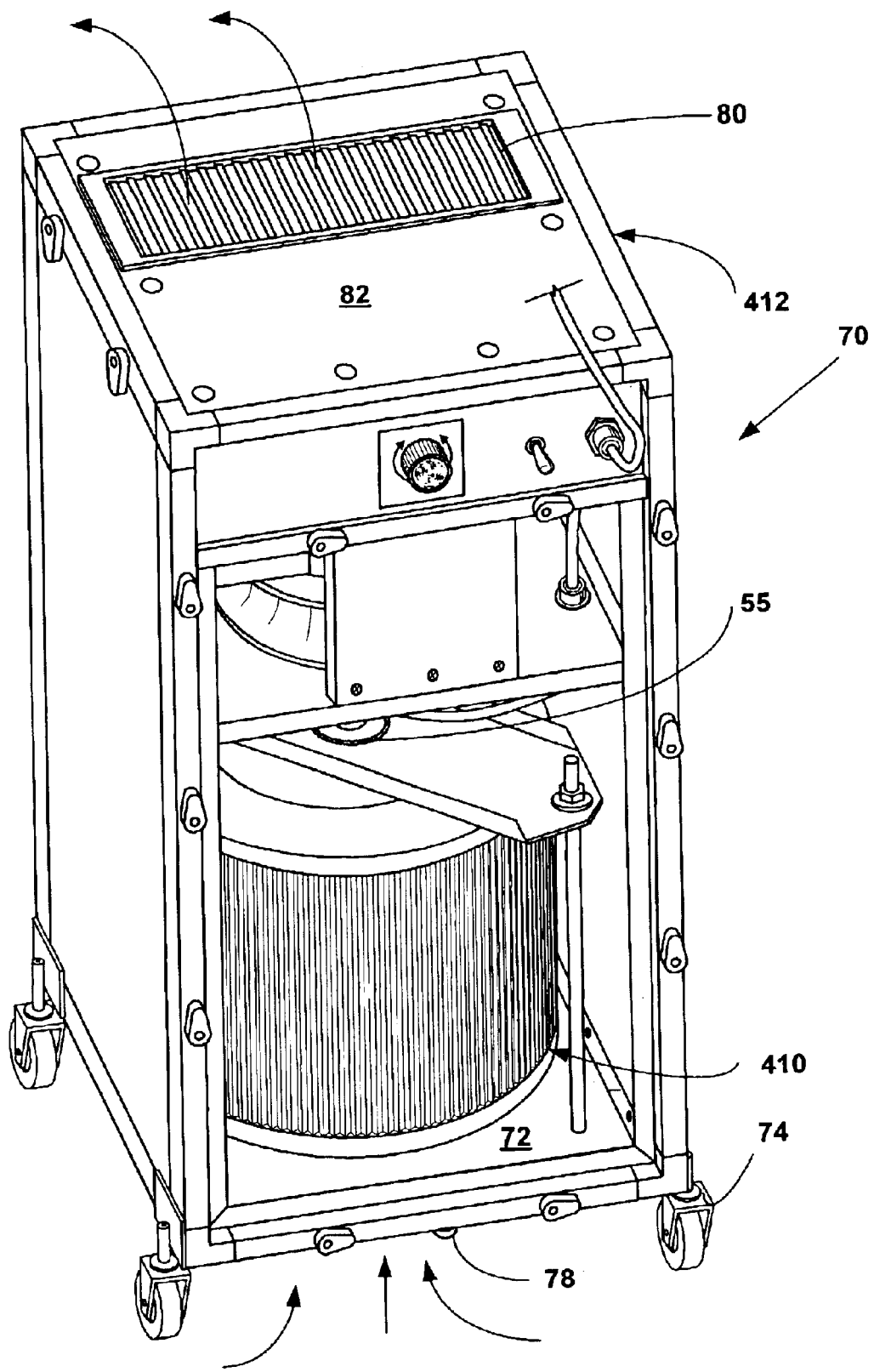
FIG. 4 is a front perspective view of an exemplary embodiment of the invention suitable for use as a stand alone room air purifier.

Turning now to the embodiment illustrated in FIG. 4, the combination filter and UV lamp assembly 410 can also be used in a room air purification unit 70. For this purpose, the housing 412 is used in an upright position as shown in FIG. 4. The housing 412 can be constructed using a frame and panel assembly like the one used in the above described inline unit, with a few modifications. For example, a base plate 72 is used instead of the end wall 18 for supporting the combination filter and ultraviolet lamp assembly 410. The air ingress opening (not shown) is provided in the base plate 72. Casters 74 are mounted to the bottom outside corners of the housing 412 for ease in moving the unit 70. The casters 74 also serve to elevate the unit above the floor to provide adequate space for air ingress to the unit 70. To keep large particulates out of the unit 70, a pre-filter (not shown) can conveniently be mounted beneath the base plate 72. In this way, changing the pre-filter involves merely reaching under the unit and rotating swivel retainers or panel blockers 78 to remove the old pre-filter and replace it with a fresh one. Of course a pre-filter could be added to the embodiment of FIGS. 1 and 2, if desired, to filter out particulates before they enter the housing 412.

The other change from the embodiment of FIGS. 1 and 2 to adapt the invention for use as a room air purifier is replacing the duct collar with an outlet vent 80. Although in the embodiment illustrated in FIG. 4 the outlet vent 80 is shown mounted in top end panel 82, as can be appreciated, the outlet vent 80 can be placed in any convenient location in the housing that is downstream of the combination filter and ultraviolet lamp assembly 410 and motor assembly 430. The outlet vent can be provided with adjustable louvers as desired for directing purified air to desired areas of a room.

In the embodiments discussed above, the fan and motor assembly 30 is arranged to draw air through the air ingress panel 18 for the air handling system embodiment or through base plate 72 for the room air purifier embodiment and through the housing 12 to deliver purified air to the outlet end such as the air egress panel 20 or through the outlet vent 80.

Figure 5:
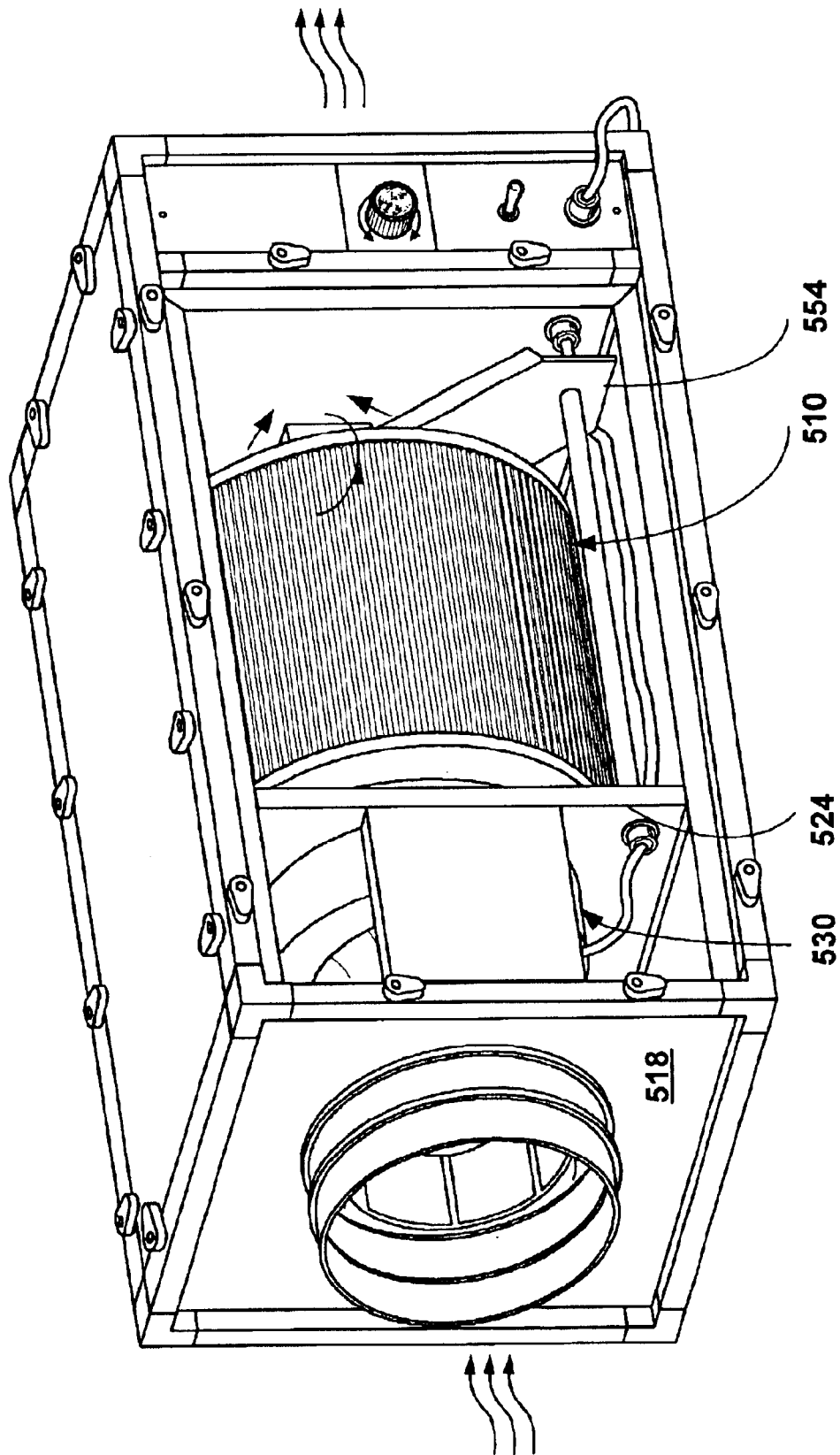
FIG. 5 is a side perspective view of an alternative arrangement of filter and fan suitable for mounting within the duct of an air handling system.

Alternatively, as shown in FIG. 5, the arrangement of fan and filter could be reversed in the in-line embodiment with the same basic components so that the fan would blow air into the filter cavity rather than drawing it into the filter cavity. With reference to FIG. 5, combination filter and lamp assembly 510 is mounted to housing divider plate 524 and fan assembly 530 is mounted to housing air ingress end panel 518. Bracket 554 can then compressibly mount the filter and lamp assembly 510 to the divider plate 524.

Figure 6:
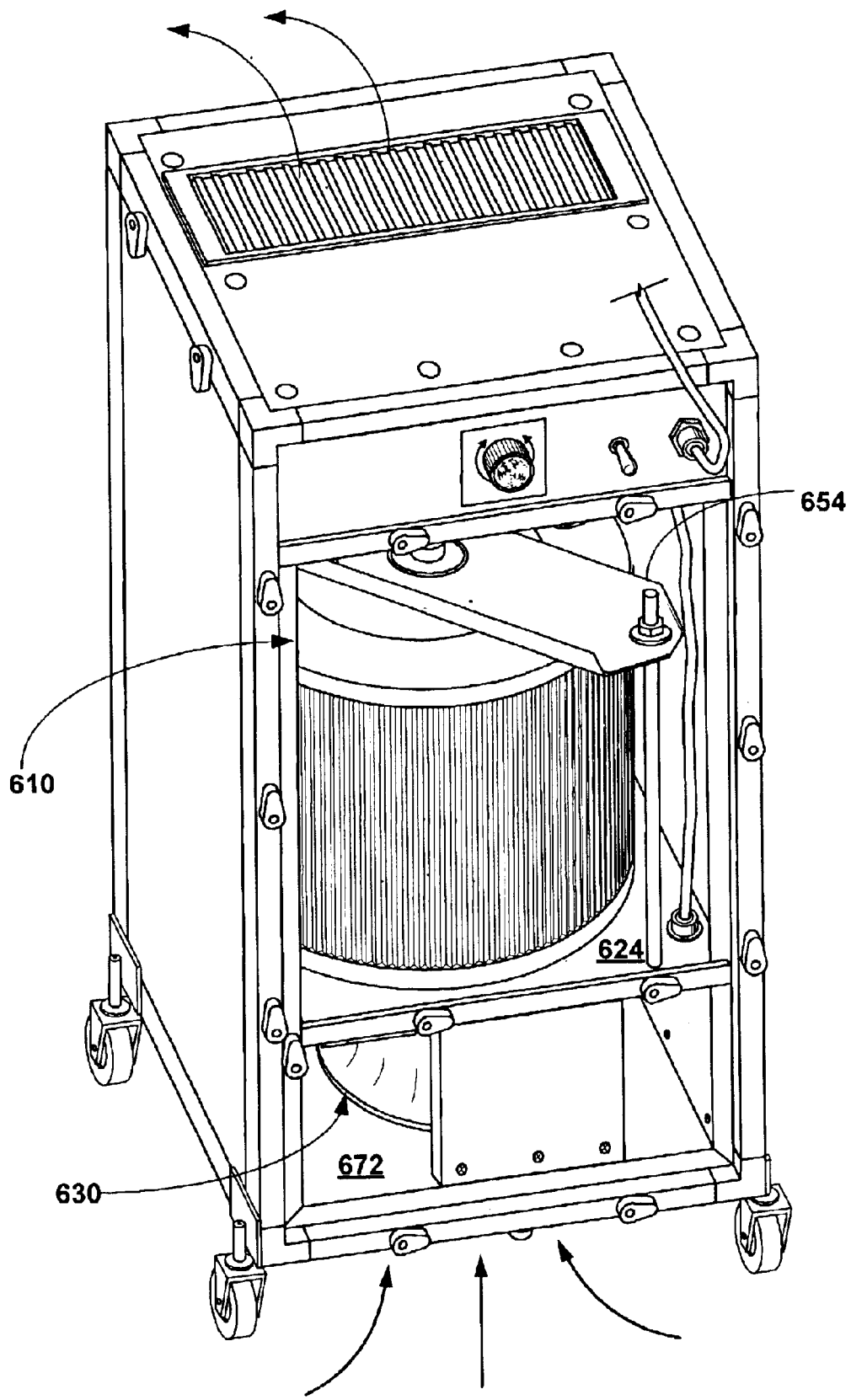
FIG. 6 is a front perspective view of an alternative arrangement of filter and fan suitable for use as a stand alone room air purifier.

Similarly, as shown in FIG. 6, the filter and fan components can be similarly repositioned in the room air purifier embodiment, where combination filter and lamp assembly 610 is mounted to housing divider plate 624 and fan assembly 630 is mounted to housing base plate 672. Bracket 654 can then compressibly mount the filter and lamp assembly 610 to the divider plate 624. The choice of arrangement of fan and filter would depend on the requirements and constraints of the air handling system in which the air purification unit is to be installed. With either a positive or negative pressure system, by mounting a UV lamp inside the cavity formed by the tubular filter medium 40 and moving air into that cavity with its only exit passage being through the medium 40, all contaminants in the air stream and those captured on the filter medium are constantly exposed to UV radiation for effectively killing all in the air stream before they exit the air purifier.

As can be appreciated, the choice of filter medium, lamp illumination and fan assembly design as well as the size and configuration of the housing depend on the particular configuration and air flow requirements of the air handling system in which the combination filter and UV lamp assembly 10 will be installed. The level and nature of anticipated contamination to be removed from the air stream are also considerations that go into the choice of components of the system. UV lamp assemblies suitable for use in the present invention are available from several vendors, including International Environmental Corporation and Steril-Aire, Inc., in a range of killing powers starting at about 120 microwatts per square centimeter. Cartridge type HEPA and ULPA filters suitable for use in the present invention are available from a large number of vendors. A pleated filter is best suited for use in the invention due to its increased effective filtering surface area and structural rigidity. Suitable fan and motor assemblies are commercially available from many vendors with a wide range of air moving capabilities. For a room air purifier unit, a fan flow rate of about 500 cfm (cubic feet per minute) will provide 12 air changes per hour in a 15×20×8 ft room or 6 air changes per hour in a 30 foot by 20 foot by 8 foot room. A fan flow rate of about 1000 cfm will provide 12 air changes per hour in a 20×30×8 ft room, and 6 air changes per hour in a 40×30×8 foot room. As practiced, the embodiments use a backward inclined (non overloading wheel design) fan.

It is recommended that the combination filter and lamp assembly 10 of the present invention be replaced before the end of the useful life of the UV lamp to assure that UV illumination is at all times working to kill contaminants on the inside of the filter. With the above described filter and lamp, replacement once a year under normal operating conditions should be adequate to assure both constant UV illumination and adequate air flow through the filter at all times up through replacement. In this way, when the combination filter and ultraviolet lamp assembly 10 is removed for replacement, there should be little or no concern for the safety of persons handling the removal.

As can now be appreciated, the purification unit of the present invention can be readily adapted for use as a small room air filtration stand alone unit, for use in hospital isolation room systems as well as any large or small air handling system, without departing from the spirit of the invention. Although illustrative embodiments of the invention have been shown and described, a wide range of modification, changes and substitution is contemplated in the foregoing disclosure. In some instances, some features of the present invention may be employed without a corresponding use of the other features. Accordingly, it is appropriate that the appended claims be construed broadly and in a manner consistent with the scope of the invention.

What is claimed is:

1. An air purification apparatus comprising:
   a combination filter and UV lamp assembly comprising:
      a UV lamp including a bulb, fixture and power connection;
      a filter medium mounted between first and second opposing end plates wherein the-first-end plate includes an opening therethrough for ingress of an air stream and the second end plate includes an opening therein sized for receiving the UV lamp bulb and for holding the UV lamp fixture in air sealing engagement with the second end plate; and
      means for removably securing the fixture of the UV lamp to the second filter mounting end plate such that the lamp bulb is positioned within and surrounded by the filter medium and the power connection is accessible from outside of the assembly;
   an imperforate housing including a first end wall and a second end wall wherein the first end wall has an opening therethrough for ingress of an air stream into the housing and the second end wall has an opening-therethrough for egress of the air stream from the housing; and
   means for removably mounting the combination filter and UV lamp assembly within the housing with the air intake opening of the first end plate of the assembly in line with the air stream ingress opening of the first end wall of the housing.

2. The air purification apparatus of claim 1 further comprising a gasket and wherein the housing includes at least one removable sidewall and wherein the means for removably mounting the combination filter and UV lamp assembly includes a bracket and threaded rod or a spring latch assembly for securing one of the opposing end plates of the combination filter and UV lamp assembly in compression against one of the first and second housing end walls with the gasket positioned between the one housing end wall and the one filter end plate.

3. The air purification apparatus of claim 1 further comprising a gasket and wherein the housing includes at least one removable sidewall and wherein the means for removably mounting the combination filter and UV lamp assembly includes a bracket and threaded rod assembly for securing one of the opposing end plates of the combination filter and UV lamp assembly in compression against one of the first and second housing end walls with the gasket positioned between the one housing end wall and the one filter end plate.

4. The air purification apparatus of claim 1 wherein the filter medium is selected from the group consisting of HEPA and ULPA filters.

5. The air purification apparatus of claim 1 further comprising a fan assembly mounted within the housing for moving air through the housing from the first to the second housing end walls.

6. The air purification apparatus of claim 3 wherein the fan assembly is mounted within the housing upstream of the combination filter and UV lamp assembly.

7. The air purification apparatus of claim 3 wherein the fan assembly is mounted within the housing downstream of the combination filter and UV lamp assembly.

8. The air purification apparatus of claim 3 wherein the fan assembly includes a backward inclined fan.

9. An air purification apparatus comprising:
   a housing having an air inlet end and an air outlet end;
   a fan assembly mounted within the housing adjacent the air outlet end of the housing; and
   a combination filter and UV lamp assembly mounted within the housing in air sealing engagement with the air inlet end of the housing, wherein the combination filter and UV lamp assembly is a cylinder comprising a filter medium comprising sidewalls of the cylinder, and first and second end plates comprising end walls of the cylinder, wherein the first cylinder end wall is a plate having an opening therein for ingress of air, and the second cylinder end wall is a plate having means therein for mounting the UV lamp assembly;
   wherein the UV lamp assembly includes a UV lamp, a fixture for mounting and supplying power and a power connector; and
   wherein the means for mounting the UV lamp assembly to the cylinder includes means for securing the assembly in air sealing engagement with the second end wall with the UV lamp extending into and along the axis of the cylinder with the power connector extending outside of the cylinder.

10. The apparatus of claim 9 wherein the filter medium is selected from the group comprising pleated HEPA and ULPA filters.

11. The apparatus of claim 9 wherein the fan assembly includes a backward inclined fan.

12. The apparatus of claim 9 wherein the housing includes a bottom wall, further comprising casters mounted adjacent the outside corners of the housing bottom wall and a louvered air vent mounted within the housing downstream of both the combination filter and UV lamp assembly and the fan assembly.

13. The apparatus of claim 9 wherein the housing includes a top wall and a bottom wall, further comprising casters mounted adjacent the outside corners of the housing bottom wall and a louvered air vent mounted within the housing top wall.

14. The apparatus of claim 12 wherein the louvered air vent includes adjustable louvers.

15. An air purification apparatus comprising:
   a housing having an air inlet end and an air outlet end;
   a fan assembly mounted within the housing adjacent the air inlet end of the housing; and
   a combination filter and UV lamp assembly mounted within the housing in air sealing engagement with the air outlet end of the housing, wherein the combination filter and UV lamp assembly is a cylinder comprising a filter medium comprising sidewalls of the cylinder, and first and second end plates comprising end walls of the cylinder, wherein the first cylinder end wall is a plate having an opening therein for ingress of air, and the second cylinder end wall is a plate having means therein for mounting the UV lamp assembly;

wherein the UV lamp assembly includes a UV lamp, a fixture for mounting and supplying power and a power connector;

wherein the means for mounting the UV lamp assembly to the cylinder includes means for securing the assembly in air sealing engagement with the second end wall with the UV lamp extending into and along the axis of the cylinder with the power connector extending outside of the cylinder; and wherein the UV lamp is configured to transmit UV light directly onto the filter medium.

16. The apparatus of claim 15 wherein the filter medium is selected from the group comprising pleated HEPA and ULPA filters.

17. The apparatus of claim 15 wherein the fan assembly includes a backward inclined fan.

18. The apparatus of claim 15 wherein the housing includes a bottom wall, further comprising casters mounted adjacent the outside corners of the housing bottom wall and a louvered air vent mounted within the housing downstream of both the combination filter and UV lamp assembly and the fan assembly.

19. The apparatus of claim 15 wherein the housing includes a top wall and a bottom wall, further comprising casters mounted adjacent the outside corners of the housing bottom wall and a louvered air vent mounted within the housing top wall.

20. The apparatus of claim 18 wherein the louvered air vent includes adjustable louvers.

21. The air purification apparatus of claim 1 further comprising a gasket and wherein the housing includes at least one removable sidewall and wherein the means for removably mounting the combination filter and UV lamp assembly includes a bracket and spring latch assembly for securing one of the opposing end plates of the combination filter and UV lamp assembly in compression against one of the first and second housing end walls with the gasket positioned between the one housing end wall and the one filter end plate.

22. An air purification apparatus comprising:

a combination filter and UV lamp assembly consisting essentially of a UV lamp defining an interior of the assembly, and a filter medium exterior to the UV lamp;

wherein the UV lamp is configured to transmit UV light directly onto the filter medium; and wherein the apparatus is configured for airflow from the interior of the combination filter and UV lamp assembly to the exterior of the combination filter and UV lamp assembly.

23. The air purification apparatus of claim 22, further comprising a housing, the combination filter and UV lamp assembly mounted within the housing.

24. The air purification apparatus of claim 23, further comprising a fan assembly mounted within the housing adjacent the combination filter and UV lamp assembly.

* * * * *